US00PP29385P3

(12) United States Plant Patent
Stemkens

(10) Patent No.: US PP29,385 P3
(45) Date of Patent: Jun. 12, 2018

(54) ***VERBENA* PLANT NAMED 'VEAZ0030'**

(50) Latin Name: *Verbena hybrida*
Varietal Denomination: VEAZ0030

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/330,466

(22) Filed: Sep. 23, 2016

(65) Prior Publication Data

US 2017/0150669 P1 May 25, 2017

(30) Foreign Application Priority Data

Nov. 19, 2015 (EM) ..... 2015/2725

(51) Int. Cl.
*A01H 5/02* (2018.01)

(52) U.S. Cl.
USPC ..... Plt./308

(58) Field of Classification Search
USPC ..... Plt./308
CPC ..... A01H 5/02; A01H 5/00
See application file for complete search history.

(56) References Cited

U.S. PATENT DOCUMENTS

PP23,049 P2 * 9/2012 Westhoff ..... A01H 5/02
Plt./308

OTHER PUBLICATIONS

Syngenta Flowers Lanai Red Star 2017, retrieved on Sep. 19, 2017, retrieved from the Internet at https://www.syngentaflowers-us.com/product/flower/70060815, 2 pp. (Year: 2017).*
Malmborg's Greenhouse Spring 2017 Rooted Cuttings, retrieved on Mar. 1, 2018, retrieved from the Internet at https://issuu.com/erin2350/docs/2017_catalog_online, pp. cover page, 70, 75-78, 80. (Year: 2016).*

* cited by examiner

*Primary Examiner* — June Hwu
(74) *Attorney, Agent, or Firm* — Dale Skalla

(57) ABSTRACT

A new *Verbena* plant named 'VEAZ0030' particularly distinguished by the large sized inflorescences, scarlet flowers with a peach starpattern, medium green, undivided leaves, and a trailing plant habit.

1 Drawing Sheet

Latin name of the genus and species of the plant claimed: *Verbena hybrida.*

Varietal denomination: 'VEAZ0030'.

BACKGROUND OF THE NEW PLANT

The present invention comprises a new *Verbena*, botanically known as *Verbena hybrida*, and hereinafter referred to by the variety name 'VEAZ0030'.

'VEAZ0030' is a product of a planned breeding program. The new cultivar has large sized inflorescences, scarlet flowers with a peach starpattern, medium green, undivided leaves and a trailing plant habit.

'VEAZ0030' originated from mutation found in June 2012 in a greenhouse in Enkhuizen, The Netherlands. The parent plant was 1453-3 with smaller red flowers.

'VEAZ0030' was selected as one flowering cutting of the stated plant in June 2012 and immediately reproduced.

The first act of asexual reproduction of 'VEAZ0030' was accomplished when stem tip cuttings were propagated in June 2012 in a greenhouse in Enkhuizen, The Netherlands.

BRIEF SUMMARY OF INVENTION

Horticultural examination of plants grown from cuttings of the plant initiated in the fall of 2011, and continuing thereafter, has demonstrated that the combination of characteristics as herein disclosed for 'VEAZ0030' are firmly fixed and are retained through successive generations of asexual reproduction.

'VEAZ0030' has not been observed under all possible environmental conditions. The phenotype may vary significantly with variations in environment such as temperature, light intensity, and day length.

A Plant Breeder's Right for this cultivar was applied for in the European Union (CPVO-Community Plant Variety Office) on Nov. 19, 2015 and assigned application number 2015/2725.

'VEAZ0030' has not been made publicly available prior to the effective filing date of this application, notwithstanding any disclosure that may have been made less than one year prior to the effective filing date of this application by the inventor or another who obtained 'VEAZ0030' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPH

The accompanying photographic drawing shows typical flower and foliage characteristics of 'VEAZ0030' with colors being as true as possible with an illustration of this type.

Figure 1:
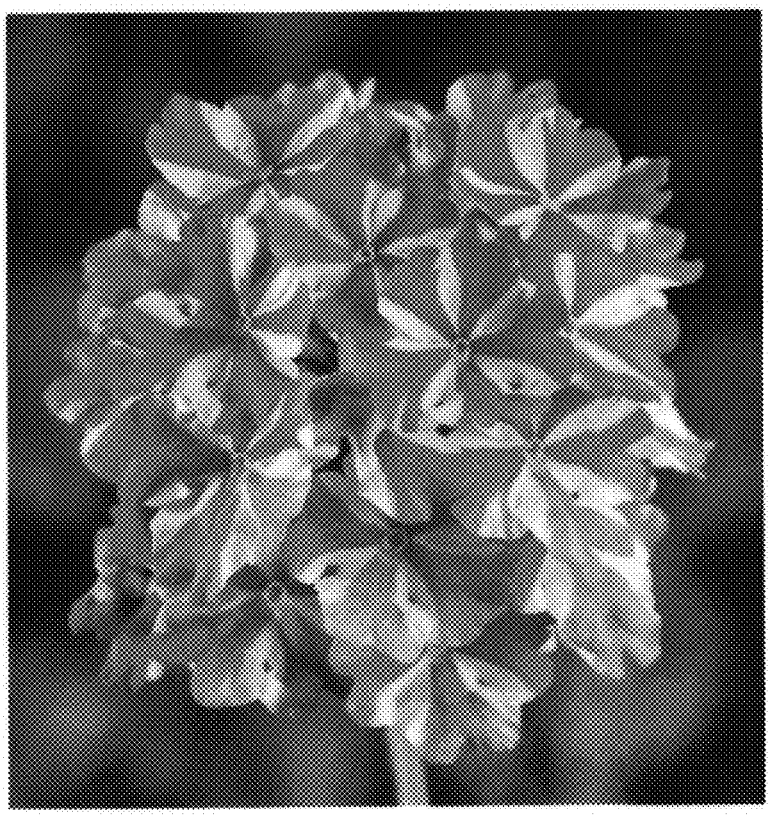
Figure 2:
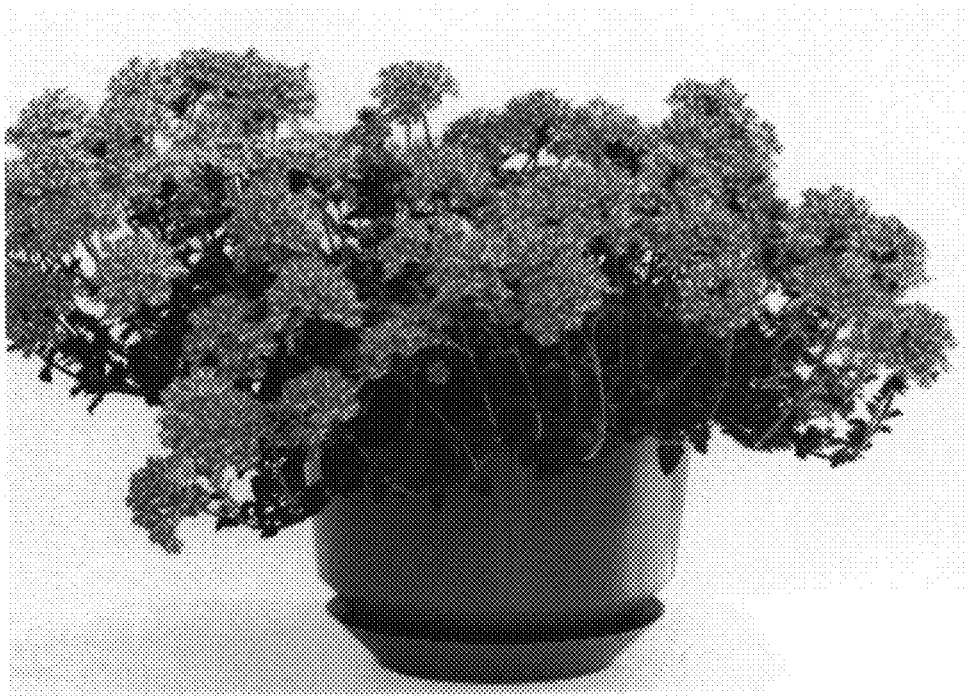

The photographic drawing in FIG. 1 shows a close view of an inflorescence of the new plant, and in FIG. 2 a whole flowering plant.

The aforementioned photograph was taken in July 2016 in Andijk, The Netherlands. The plants were about 12 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0030' AND MOST SIMILAR VARIETIES

| | 'VEAZ0030' | 'Voodoo Red Star' (Wesverevostar PP23,049) | 'VEAZ0033' US 2017/0150668 P1 |
|---|---|---|---|
| Flower color: | Scarlet with a peach star | Scarlet red with a dark peach star | Red rose with a peach star |
| Flower, size: | Larger | Smaller | Larger |
| Leaf, width: | Large | Medium | Medium |
| Mildew susceptibility: | Not susceptible | Very Susceptible | Not Observed |

Plant:

*Form, growth and habit.*—Herbaceous, trailing and free-branching.

*Plant height.*—18.0 cm.

*Plant height (inflorescence included).*—22.0 cm.

*Plant width.*—56.0 cm.

Roots:

*Number of days to initiate and produce roots.*—11-13 days at about 23 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 138B.

*Immature, leaf color, lower surface.*—RHS 137C.

*Mature, leaf color, upper surface.*—RHS 137A.

*Mature, leaf color, lower surface.*—RHS 137D.

*Length.*—Approximately 3 cm.

*Width.*—3.5-4 cm.

*Shape.*—Hastate.

*Base shape.*—Obtuse.

*Apex shape.*—Obtuse.

*Margin.*—Entire.

*Texture, upper surface.*—Pubescent.

*Lower surface.*—Pubescent.

*Color of veins, upper surface.*—RHS 145C.

*Color of veins, lower surface.*—RHS 145B.

*Pattern of veining.*—Pinnate.

*Petiole color.*—RHS 145B.

*Petiole length.*—0.6 cm.

*Petiole width.*—0.5 cm.

*Texture.*—Hirsute.

Stem:

*Branching characteristics.*—Side branches develop potentially at each node.

*Quantity of main branches per plant.*—9 to 12.

*Color of stem.*—RHS 143A.

*Stem length.*—About 14.0-26.0 cm.

*Stem width.*—About 0.3 cm.

*Length of internodes.*—About 2.5 to 3 cm.

*Texture.*—Hirsute.

*Color of peduncle.*—RHS 138C.

*Length of peduncle.*—From 2.0 to 4.0 cm.

*Peduncle diameter.*—0.3 cm.

*Texture.*—Canescent, also short, transparent. glandular hairs.

Inflorescence:

*Type.*—Umbel-like, but actually a spike, umbrella-shaped.

*Blooming habit.*—Flowers continuously during the summer months.

*Lastingness of individual blooms on the plant.*—About 4-5 days in the greenhouse.

*Fragrance.*—None.

*Number of inflorescences per plant.*—49 at various stages at development.

*Horizontal diameter of inflorescence.*—5.9-6.9 cm.

*Depth of inflorescence.*—3.8 cm.

*Number of florets and buds per inflorescence.*—Approximately 38-40.

Bud:

*Color.*—RHS N155A.

*Length.*—0.4 cm (corolla only).

*Width.*—0.3 cm.

*Shape.*—Tubular with bulbous apex.

Floret:

*Form.*—Sessile; salver-shaped, composed of 5 partly fused petals with a base of a narrow tube.

*Immature color, upper surface.*—RHS 52A with a starpattern of RHS 38B.

*Immature color, lower surface.*—RHS 39A with a starpattern of RHS 38C.

*Mature color, upper surface.*—RHS 52B with a starpattern of RHS 38B.

*Mature color, lower surface.*—RHS 39A with a starpattern of RHS 38C.

*Floret diameter.*—3.5 cm.

*Floret length (depth).*—2.9 cm.

*Petal length.*—1.4 cm.

*Petal width.*—1.5 cm.

*Shape.*—Obcordate.

*Apex shape.*—Emarginate.

*Margin.*—Entire.

*Petal texture, upper surface.*—Papillose; a little glandular hair.

*Petal texture, lower surface.*—Papillose, pubescent.

*Corolla tube length.*—2.4 cm.

*Corolla tube width.*—0.3 cm.

*Corolla tube color inside.*—RHS 39B.

*Tube color outside.*—RHS 46C.

*Corolla texture, inside.*—Pubescent.

*Corolla texture, outside.*—Canescent, lower part glabrous.

*Throat hair color.*—RHS 155D but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 143B.

*Length of sepals.*—1.1 cm.

*Width of sepals.*—0.2 cm.

*Sepal shape.*—Fused, linear.

*Apex shape.*—Acute.

*Margins*.—Entire.
*Texture*.—Fensely covered with very short glandular hair.

Reproductive organs:
*Gynoecium*.—
*Pistil*.—1.
*Pistil length*.—1.5 cm.
*Style color*.—RHS N144B.
*Style length*.—1.5 cm.
*Stigma color*.—RHS 144A.
*Ovary color*.—RHS 144B.
*Ovary length*.—0.2 cm.
*Ovary width*.—0.1 cm.
*Androecium*.—
*Stamens*.—Anthers and filaments fused to upper half of corolla tube; four anthers with two pollen sacs per anther.
*Color of filaments*.—RHS 151D.
*Filament length*.—0.2 cm.
*Anther color*.—RHS 151C.
*Anther length*.—0.1 cm.
*Pollen amount*.—None observed.

Fertility/seed set: Neither seed nor fruit production has been observed to date.

Disease/pest resistance: Resistance to pathogens and pests common to *Verbena* has not been observed.

What is claimed is:

1. A new and distinct variety of *Verbena* plant named 'VEAZ0030' substantially as illustrated and described herein.

* * * * *